(12) United States Patent
Howard

(10) Patent No.: US 6,176,860 B1
(45) Date of Patent: Jan. 23, 2001

(54) ORTHOPAEDIC FIXATOR

(75) Inventor: Charles Howard, Omer (IL)

(73) Assignee: Hadasit Medical Research Services & Development Company, Ltd., Jerusalem (IL)

( * ) Notice: Under 35 U.S.C. 154(b), the term of this patent shall be extended for 0 days.

(21) Appl. No.: 09/077,756

(22) PCT Filed: Jul. 24, 1996

(86) PCT No.: PCT/IB96/00785

§ 371 Date: Jun. 11, 1998

§ 102(e) Date: Jun. 11, 1998

(87) PCT Pub. No.: WO97/03620

PCT Pub. Date: Feb. 6, 1997

(30) Foreign Application Priority Data

Jul. 24, 1995 (IL) .......................................... 114714

(51) Int. Cl.[7] .................................................. A61B 17/64
(52) U.S. Cl. ................................................. 606/54; 606/57
(58) Field of Search .................. 606/54, 57, 58, 606/59, 105

(56) References Cited

U.S. PATENT DOCUMENTS

| | | | | |
|---|---|---|---|---|
| 4,312,336 | * | 1/1982 | Danieletto et al. | 606/57 |
| 4,475,546 | * | 10/1984 | Patton | 606/57 |
| 4,621,627 | * | 11/1986 | DeBastiani et al. | 606/57 |
| 4,628,919 | * | 12/1986 | Clyburn | 606/55 |
| 4,714,076 | * | 12/1987 | Comte et al. | 606/57 |
| 4,730,608 | * | 3/1988 | Schlein | 606/57 |
| 4,782,842 | * | 11/1988 | Fletti, Jr. | 606/54 |
| 5,207,676 | * | 5/1993 | Canadell et al. | 606/54 |
| 5,320,622 | * | 6/1994 | Faccioli et al. | 606/58 |
| 5,556,398 | * | 9/1996 | Bagits et al. | 606/59 |
| 5,688,271 | * | 11/1997 | Faccioli et al. | 606/54 |
| 5,803,924 | * | 9/1998 | Oni et al. | 606/54 |
| 5,928,230 | * | 7/1999 | Tosic | 606/57 |
| 5,941,877 | * | 8/1999 | Viegas et al. | 606/55 |
| 6,022,349 | * | 2/2000 | McLeod et al. | 606/58 |
| 6,024,745 | * | 2/2000 | Faccioli et al. | 606/54 |
| 6,036,691 | * | 3/2000 | Danieletto et al. | 606/57 |

FOREIGN PATENT DOCUMENTS

| | | | |
|---|---|---|---|
| 0 314 021 | | 5/1989 | (EP) . |
| 0 424 292 | | 4/1991 | (EP) . |
| 1 206 411 | | 2/1960 | (FR) . |
| 2258155 | * | 3/1993 | (GB) .................................... 606/54 |
| 2633345 | * | 3/1993 | (FR) .................................... 606/59 |

\* cited by examiner

*Primary Examiner*—Paul J. Hirsch
*Assistant Examiner*—Michael B. Priddy
(74) *Attorney, Agent, or Firm*—McDermott, Will & Emery

(57) ABSTRACT

The invention provides a dynamic external fixator, including an elongate body having an axial bore accommodating, in a first portion thereof, at least part of a first member of a universal joint and, in a second portion thereof, a linear guide element, a first arm having an end portion carrying the second member of said universal joint. The arm is provided with a plurality of apertures for the traversing therethrough of bone pins. There is also provided a second arm integral with, or fixedly attached to, a member of the guide element and provided with a plurality of apertures for the traversing therethrough of bone pins, and a spring accommodated in the axial bore of the body and bearing, on the one hand, against the first member of the universal joint and, on the other, at least indirectly, against the guide element, thereby opposing forces acting on the second arm.

29 Claims, 5 Drawing Sheets

ORTHOPAEDIC FIXATOR

The present invention relates to an orthopedic fixator, more particularly, to a dynamic external fixator for osteosynthesis.

Fractures of long bone constitute about 30% of trauma-related disabilities that, in the U.S.A., affect more than 400,000 people per year, at a cost to the American economy of an order of tens of billions of dollars.

Recent evaluation of the accumulating clinical evidence clearly indicated that stabilization of all major unstable fractures by external or internal fixation within the first 24 hours in a patient sustaining multiple injuries decreases the duration of ventilatory support required, decreases mortality, decreases the time spent in intensive-care units, decreases the incidence of adult respiratory distress syndrome, reduces the incidence of multi-organ failure and late sepsis, reduces the incidence of complication related to the fractures and improves fracture outcome, and decreases the length of hospitalization and medical costs. In addition, early fixation greatly reduces fracture pain, facilitates access to the patient (essential in the case of open fractures), and simplifies nursing care. The need for forced recumbency is reduced, together with the risk of pressure sores, pulmonary infection, pulmonary embolus, etc.

External fixation is a safe and reliable method of achieving osseous stability in long bones. The advantages of external fixation are versatility, ease of application with minimum operative time and trauma (of great importance in the early stage after major trauma), and maintenance of access to any concurrent soft tissue injury. While in the past, rigidity of the fracture was considered advantageous and many of the available devices are built to eliminate all movement at the fracture site, it is now generally accepted that some movement at the fracture site is essential for good fracture healing; hence, dynamization of the fracture is desirable. However, known fixators that do allow dynamization, permit only compression, and this only on the "micromovement" scale of 0.2–0.6 mm. Thus, only stable fractures are suitable for application of present dynamic fixators. All unstable fractures have to have a static fixator until the healing of the fracture has progressed to the stage when the fracture is stable enough for dynamization. Yet it is precisely this early stage which requires the micromovements to induce sufficient healing to produce this stability.

Existing fixators described in UK Application No. GB 2,104,782 A and PCT Publication No. WO 91/11149, are designed in light of the assumption that "excessive movement will produce non-union." Recent experience has, however, shown the bone to be not only forgiving of "detectable" movements of several millimeters in the early stage, but that such early movements are actually desirable. The all-important callus response dying away with time, prior art fixators thus miss the optimal period for stimulating callus formation.

It is thus one of the objects oaf the present invention to provide a relatively inexpensive device that, while permitting immediate weight bearing by patients also with unstable fractures, will produce an axial compression/distraction cycle automatically controlled by the patient's own walking rhythm, a cycle that promotes the early formation of the primary callus so important for the rapid progress of the healing process.

According to the invention, the above object is achieved by providing a dynamic external fixator comprising an elongate body having an axial bore accommodating, in a first portion thereof, at least part of a first member of a universal joint and, in a second portion thereof, a linear guide means; a first arm having an end portion carrying the second member of said universal joint, said rod being provided with a plurality of apertures for the traversing therethrough of bone pins; and a second arm integral with, or fixedly attached to, a member of said guide means and provided with a plurality of apertures for the traversing therethrough of bone pins, and spring means accommodated in said axial bore of said body and bearing, on the one hand, against said first member of said universal joint and, on the other, at least indirectly, against said guide means, thereby opposing forces acting on said second arm.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figure 1:
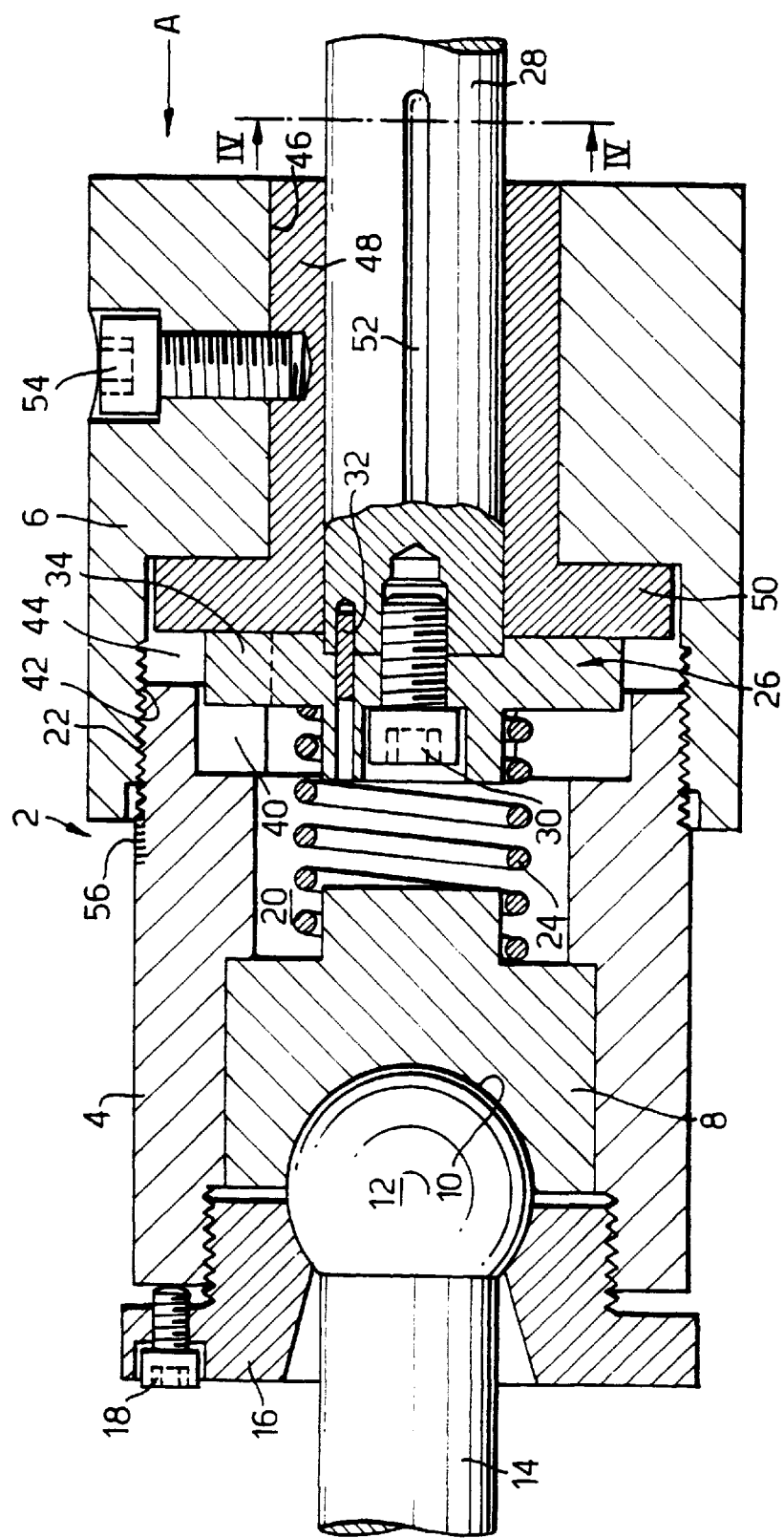
FIG. 1 is a cross-sectional view of a first embodiment of the fixator according to the invention.

Referring now to the drawings, there is seen in FIG. 1 a substantially cylindrical two-member body 2 comprised of a first member 4 and second member 6. At one of its ends, member 4 is provided with an insert 8 configured as a substantially semi-spherical socket 10 of a ball-and-socket joint. Socket 10 can also be an integral part of member 4.

The spherical head 12 of a first arm 14, details of which will be discussed further below, fits into socket 10. A locking ring 16, complementing the spherical socket 10, can be screwed into member 4 to immobilize the ball-and-socket joint, with a locking screw 18 securing the locking position of ring 16.

Figure 2:
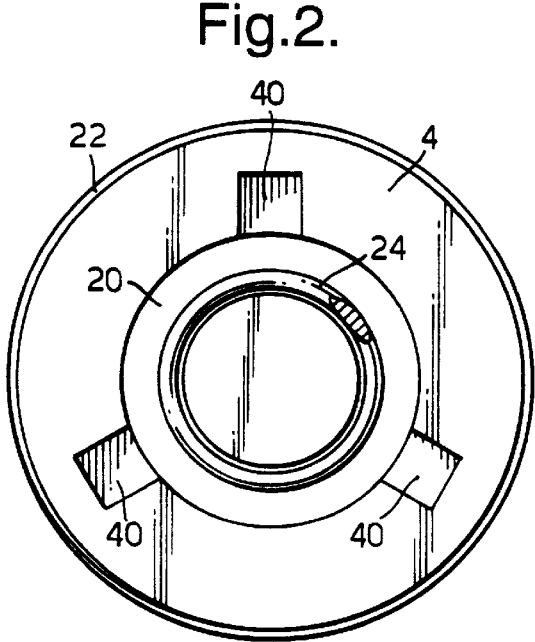
FIG. 2 is a view of the spring-side end of the first member.

The other end of member 4, shown to better effect in FIG. 2, is provided with a central recess 20 and, at its periphery, with an external thread 22. Recess 20 accommodates a helical spring 24 that rests against insert 8 at one of its ends, and at its other end bears against a head piece 26 fixedly connected to a second arm 28 by means of screw 30 and advantageously additionally secured by a dowel pin 32. As will become clear, it is this spring that facilitates the above-mentioned compression/distraction cycle characteristic of the present invention. Also seen in FIG. 2 are three recesses 40 at an angular spacing of 120 d, the purpose of which will be presently explained.

Figure 3:
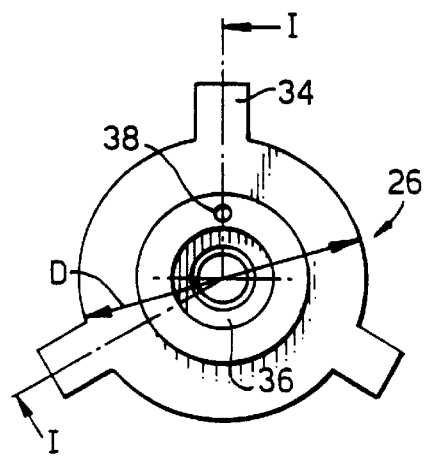
FIG. 3 is a frontal view of the head piece.

Head piece 26, shown in FIG. 1 in cross-section along plane I—I of FIG. 3, is seen in latter to be of a basically discoid shape with three prismatic projections 34. Also shown is a countersunk hole 36 for the head of screw 30 and a hole 38 for the securing pin 32. The dimensions and angular spacing of projections 34 are such that they will fit into corresponding recesses 40 in member 4, seen in both FIGS. 1 and 2, while the diameter D of the discoid body is slightly smaller than that of recess 20, so that head piece 26, when pushed by arm 28, is able to penetrate into recess 20 of member 4 against the restoring force of spring 24. Because of the good fit of projections 34 in recesses 40, the movement of head piece 26 relative to member 4, and thereby also that of arm 28, is limited to one degree of freedom in translation only.

Member 6, the second member of two-member body 2, is provided with an internal thread 42 matching external thread 22 of member 4, and can thus be joined to the latter, the overall length of two-member body 2 being adjustable by altering the length of mutual engagement of threads 22 and 42. Member 6 is also provided with a recess 44 substantially coaxial with thread 42, and a bore substantially coaxial with recess 44.

Further seen is a sleeve 48 rotatable accommodated in bore 46 of member 6 and having a shoulder 50 seated against the bottom of recess 44. Head piece 26 is pressed by spring 24 against the upper surface of shoulder 50.

Figure 4:
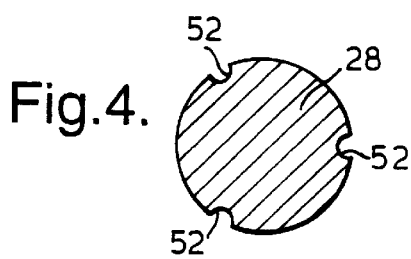
FIG. 4 is a view of the second arm, in cross-section along plane IV—IV of FIG. 1.

The purpose of sleeve 48 is to reduce the friction encountered by arm 28 when the patient, by walking, brings his weight to bear against the reduced fracture of the properly pinned bone of his broken leg. As the force acting on arm 28 is not applied in a strictly axial direction, it produces a moment that may cause skewing and even jamming, unless friction inside member 6 is reduced to a mimimum. This is achieved by using a friction-reducing element for sleeve 48, e.g., a ball spline. Such elements are commercially available and require the provision, in arm 28, of a number of tracks or races 52, typically three, in which the steel balls of the ball spline will run, as shown in the cross-sectional view of FIG. 4. Not shown in FIG. 1 are the details of the ball spline, e.g., the channels through which the balls circulate when a relative movement takes place between sleeve 48 and arm 28. The ball spline sleeve 48 also has a nearly frictionless effect on constraining the degrees of freedom of arm 28 relative to body 2 to one degree of freedom in translation only.

Figure 7:
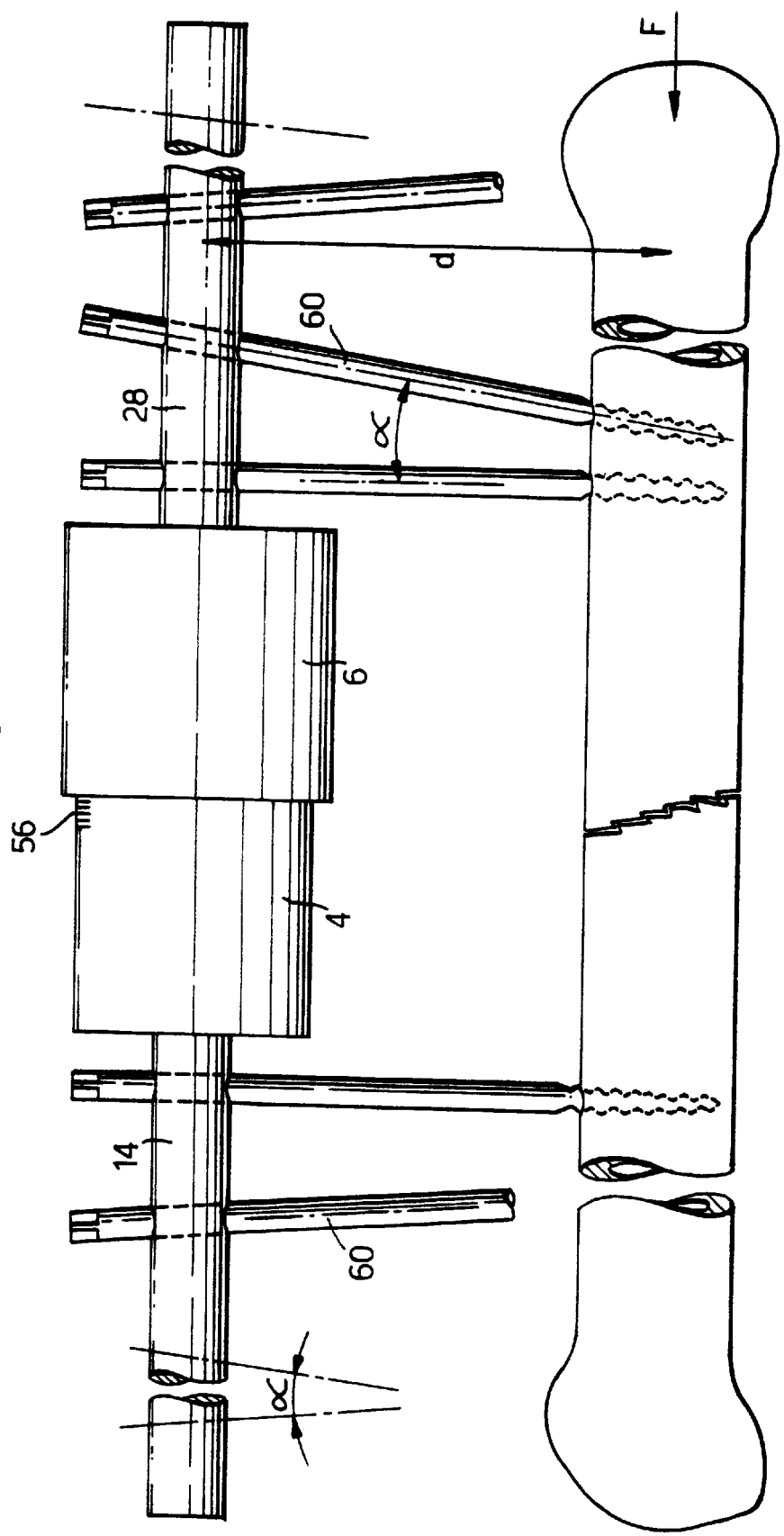
FIG. 7 is a schematic presentation of the fixator as connected to a fractured long bone.

Static compression of the fracture surfaces can be controlled by the surgeon by reducing or increasing the distance between the bone pins anchored in arm 14 and those anchored in arm 28 (see FIG. 7). This is done by first loosening locking screws 54, of which there may be several. Locking screws 54, in the position shown in FIG. 1, prevent rotary motion of member 6 relative to sleeve 48 and thereby to arm 28. Assuming threads 22 and 42 to be right-handed, a clockwise rotation of member 6, as seen in the direction of arrow A, will reduce the above distance and increase compression, while a counterclockwise rotation will increase this distance and reduce compression. A scale 56 engraved on member 4 serves for orientation and ensures reproducibility. The total range of possible movement is about 5 mm, but that range could also be increased.

Figure 5:
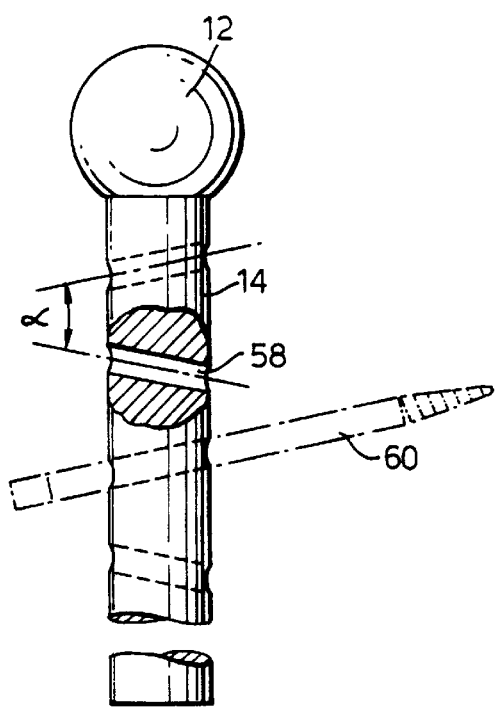
FIG. 5 shows the first arm with its spherical head and slanting holes traversing the arm.

FIG. 5 shows arm 14 with its spherical head 12. There are seen a plurality of holes 58 traversing arm 14 and accommodating bone pins 60, one of which is indicated by dash-dotted lines.

It is clearly seen that while holes 58 lie in a common median plane of arm 14, they are not perpendicular to the arm axis and include, with adjacent holes, acute angles a which, however, need not be uniform for all hole pairs. The result of this unique design feature is that once two pins 60 have been inserted into a bone fragment the fixator can no longer slide along pins 60, which would not be the case if pins 60 were parallel and perpendicular to the arm axis. While this self-locking effect should suffice to secure the position of the fixator relative to the patient's leg, the hold of the arms on pins 60 can be increased, either during operation or in the postoperative period, by means of small set screws inserted at right angles to the pins via the arms.

Figure 6:
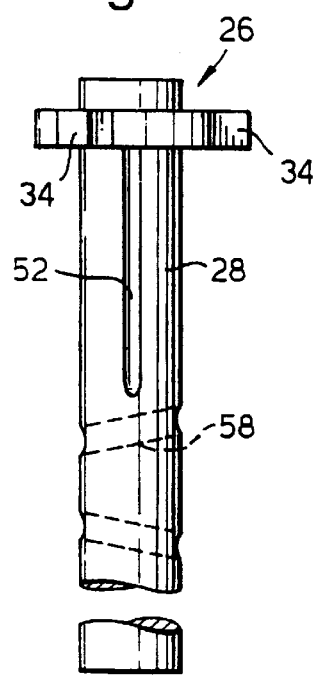
FIG. 6 shows the second arm with the head piece attached.

FIG. 6 represents arm 28 with head piece 26 in position. The above description of holes 58 in conjunction with FIG. 5, is also valid with respect to FIG. 6.

FIG. 7 illustrates the fixator according to the invention, as applied to a fractured bone. It is clearly seen that a force F, applied to the bone by ground reaction to the working patient's weight, will produce a bending moment F×d in arm 28 that will cause considerable frictional resistance to the movement of arm 28 required to compress spring 24 to counteract force F and produce the desired distraction once the patient's leg is lifted off the ground.

It is, of course, necessary to provide each fixator with a set of springs 24 of different hardness, to allow for differences of body weight between different patients.

Figure 8:
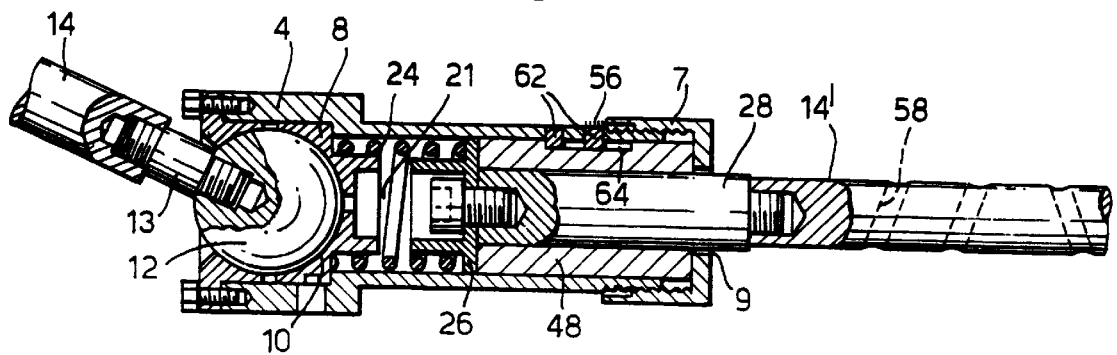
FIG. 8 is a cross-sectional view of a second embodiment of the fixator.

FIG. 8 illustrates a further embodiment of the fixator according to the invention.

There is seen body 4 having an axial bore 21 which, in a first portion thereof, accommodates insert 8, part of a universal joint, which here, as in the embodiment of FIG. 1, is a ball-and-socket joint, the ball member 12 of which is joined to arm 14 by a connector piece 13. A second portion of bore 21 slidingly accommodates a sleeve 48, the first, outer member of low-friction linear guide means, such as the ball spline of FIG. 1; the second, inner member 28 of which, as was explained in conjunction with the previous embodiment, is constrained relative to sleeve 48 to one degree of freedom in translation. Sleeve 48, in its turn, is constrained to one degree of freedom in translation relative to body 4 by means of screws 62, screwed into the wall of body 4 and entering a groove 64 in sleeve 48, thereby preventing rotary movement of sleeve 48 relative to body 4. Groove 64 is obviously long enough to permit the required translation, i.e., axial movement, of sleeve 48.

Further seen is a head or abutment piece 26, of a substantially discoid shape and fixedly attached to inner member 28 of the above-mentioned linear guide means. Head piece 26 has a diameter larger than the diameter of inner member 28 and of helical spring 24 for which it serves as an abutment. The purpose of spring 24 has been explained in conjunction with the previous embodiment.

Also shown in FIG. 8 is a thimble 7 with a central hole 9 that fits over inner guide means member 28 with clearance. Thimble 7 is provided with an internal thread which matches an external thread provided along an end portion of body 4.

It is clearly seen that when thimble 7 is turned in the clockwise sense, pressure is exerted on sleeve 28, which (provided the above thread is a right-hand thread) is pushed inwards against the restoring force of spring 24, thereby applying static compression via bone pins 60 (see FIG. 7) to the fracture. As in the embodiment of FIG. 1, scale 56 engraved on body 4 serves for orientation and facilitates reproducibility.

Arm 14' of FIG. 8 differs from arm 28 of FIG. 1, in that it is not an integral part of inner member 28 of the linear guide means, but is fixedly attached thereto.

Figure 10:
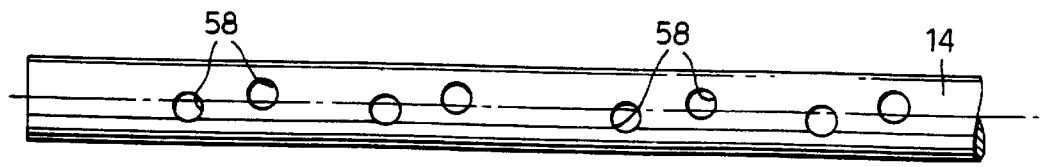
FIG. 10 is a view of the arm of FIG. 9, as seen in the direction of arrow A of FIG. 9.

A further difference resides in the fact that, while in the embodiment of FIG. 1, bone pin holes 58 lie in a common median plane M of arms 14, 28, in the embodiment of FIG. 8 the axes of holes 58 are slightly angularly offset from that plane alternatingly to one and the other side thereof, as is clearly seen in FIG. 10. This design further enhances the above-mentioned self-locking effect.

Figure 9:
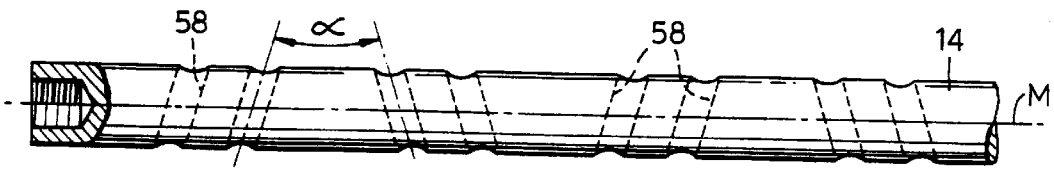
FIG. 9 shows one of the arms of FIG. 8, as seen in a direction normal to the median plane in FIG. 10.

As is seen in FIG. 9, holes 58 are preferably arranged in pairs, with the angle α included by adjacent pairs varying between 16–25°. The deviation from the median plane M, seen in FIG. 10, as advantageously about ±4°. (For reasons of simplicity, FIG. 9 represents holes 58 as if they were all located in median plane M.)

Figure 11:
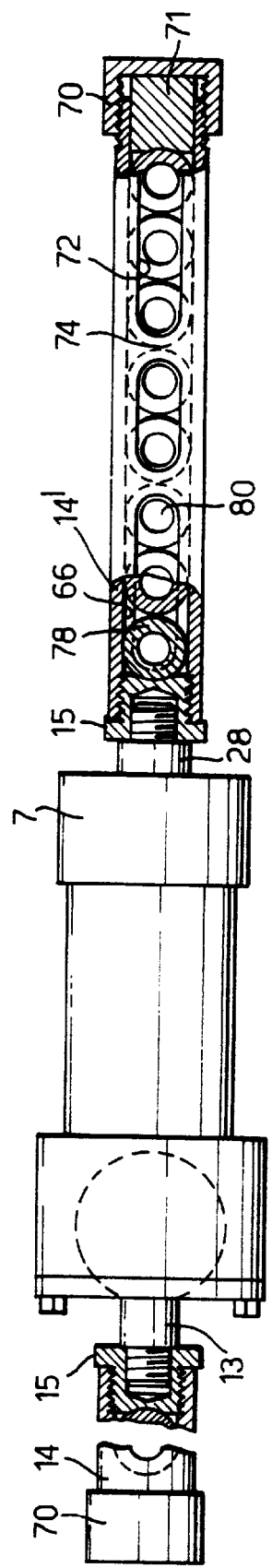
FIG. 11 illustrates yet another embodiment of the invention, in which the angular deviation of the holes, from perpendicularity relative to the arm axes and from the median plane of the arms, is steplessly variable.

While in the embodiments of FIGS. 1 and 8 bone pins 58 can assume a number of discrete angular positions only (relative to arms 14, 14', 28), the embodiment illustrated in FIG. 11 permits these positions to be steplessly varied within reasonable limits.

As seen in FIG. 11, each of the arms, in this embodiment tubular members 14, 14', is provided on one of its ends with an internal thread accommodating an adaptor 15 for connecting piece 13, respectively for the threaded end of inner ball-spline member 28, and on the other end with an external thread for a locking thinble 70, the purpose of which will be explained further below.

Tubular members 14, 14' are further provided with elongated slots 72 extending along two diagonally opposed generatrices of members 14, 14' and having widths slightly exceeding the diameter of bone pins 60. For reasons of mechanical strength, slots 72 are of limited length only, with bridge sections 74 separating adjoining slots 72. The length of the separate slots 72 will be discussed presently.

Figure 12:
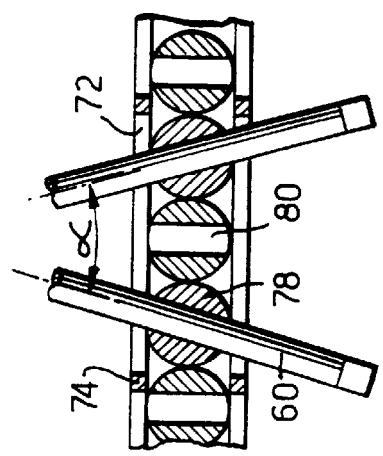
FIG. 12 is a partial view of the arm of FIG. 11, as seen in a direction perpendicular to the direction in which FIG. 11 was viewed.

Further seen in FIGS. 11, 12 is a plurality of spherical bodies 78 slidingly fitting bore 66, each of bodies 78 being provided with a diametral hole 80 of a size adapted to slidingly accommodate a bone pin 60.

For use of the fixator, tubular members 14, 14' are filled with spherical bodies 78, leaving free only a length of bore 66 for a pressure pad 71 and locking thimble 70 is mounted, without, at this stage, tightening it. The lengths and positions of slots 72 are such that they not only fully expose a discrete number of holes 80 in bodies 78, such as two or three, as in FIG. 11, but beyond that, enabling, as seen in FIG. 12, two bone pins 60 to include an acute angle α of a reasonable magnitude. In use, bone pins 60 are introduced into the patient's bone and thimble 70 is tightened, applying pressure to pad 71, which is transferred to spherical bodies 78 and, due to their elastic deformation, immobilizes bone pins 60 within bodies 78, as well as the selected angle α.

The fact that slots 72, as explained earlier, are somewhat wider than the diameter of bone pins 60, facilitates, if so desired, the angular setoff of bone pins 60 with respect to the median plane M of FIG. 10, as discussed above in conjunction with the embodiment of FIG. 8.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A dynamic external fixator, comprising:
   an elongate body having an axial bore accommodating, in a first portion thereof, at least part of a first member of a universal joint and, in a second portion thereof, a linear guide means;
   a first arm having an end portion carrying a second member of said universal joint, said arm being provided with a plurality of apertures for the traversing therethrough of bone pins; and
   a second arm integral with, or fixedly attached to, a member of said guide means and provided with a plurality of apertures for the traversing therethrough of bone pins, and spring means accommodated in said axial bore of said body and bearing, on the one hand, against said first member of said universal joint and, on the other, at least indirectly, against said guide means, thereby opposing forces acting on said second arm.

2. The fixator as claimed in claim 1, wherein said first and second arms are substantially solid rods.

3. The fixator as claimed in claim 1, wherein said first and second arms are substantially tubular members having bores therein and having free ends.

4. The fixator according to claim 1, wherein said apertures in said arms are of such configuration or orientation that at least some of said bone pins, having been introduced into, and traversed, said arms, include with said arms angles other than 90°.

5. The fixator as claimed in claim 1, wherein said first member of said universal joint is a part of a spherical socket, and said second member constitutes the ball of a ball-and-socket joint.

6. The fixator as claimed in claim 1, wherein said guide means is a low-friction linear guide unit.

7. The fixator as claimed in claim 6, wherein said linear guide unit is a two-member ball spline.

8. The fixator as claimed in claim 7, wherein the first member of said two-member ball spline is a sleeve slidingly accommodated in said body and limited by constraining means to one degree of freedom in translation relative to said body.

9. The fixator as claimed in claim 8, wherein the second member of said two-member ball spline is a shaft slidingly accommodated in said sleeve and limited by constraining means to one degree of freedom in translation relative to said sleeve.

10. The fixator as claimed in claim 8, further comprising abutment means fixedly attached to said second member of said ball spline and defining an extreme position of said first member of said ball spline relative to the second member thereof.

11. The fixator as claimed in claim 10, wherein said abutment means is substantially discoid, having a diameter larger than the external diameter of said second member of said ball spline, as well as of said spring means.

12. The fixator as claimed in claim 11, wherein said spring means is a helical compression spring mounted in said axial bore and is substantially coaxial with said second member of said ball spline.

13. The fixator as claimed in claim 5, further comprising a locking ring configured as a complementary part to said part of the spherical socket of said ball-and-socket joint and fixedly attachable to said first portion of said body for the purpose of immobilizing said ball-and-socket joint.

14. The fixator as claimed in claim 11, further comprising thimble means cooperating with said second portion of said body to control the position of said first and second members of said ball spline relative to said body, against the restoring force of said spring means.

15. The fixator as claimed in claim 14, wherein said thimble means has a rim and is provided with an internal thread matching an external thread provided on said second portion of said body.

16. The fixator as claimed in claim 15, further comprising a linear scale disposed on said body, whereby the axial position of said first member of said ball spline relative to said body is indicated, with the rim of said thimble means serving as an index.

17. The fixator as claimed in claim 1, wherein the apertures in said first and second arms are substantially cylindrical holes of a size appropriate to provide a sliding fit to said bone pins.

18. The fixator as claimed in claim 17, wherein said holes are arranged along said arms in pairs of substantially parallel holes.

19. The fixator as claimed in claim 18, wherein the axes of the holes of each pair of holes include an acute angle with the axes of an adjacent pair of holes.

20. The fixator as claimed in claim 18, wherein the axes of said holes lie in a common median plane.

21. The fixator as claimed in claim 20, wherein the axes of said holes deviate from said median plane alternatingly to one and the other side thereof.

22. The fixator as claimed in claim 3, wherein said tubular members are each provided with at least two elongated slots extending along two diagonally opposed generatrices of said tubular portions, the width of said slots being at least as large as the diameters of said bone pins.

23. The fixator as claimed in claim 22, wherein said oppositely located, elongated slots extending along said tubular members are subdivided into a plurality of pairs of oppositely located, relatively short slots, with bridge sections separating adjacent short slots, the width of said short slots exceeding the size of the diameters of said bone pins.

24. The fixator as claimed in claim 3, wherein the free ends of said tubular members are each provided with thread means of a predetermined length.

25. The fixator as claimed in claim 3, further comprising a plurality of spherical bodies, slidingly fitting the bore of said tubular member, each body being provided with a substantially diametral hole of a diameter at least as large as the diameter of said bone pins.

26. The fixator as claimed in claim 23, wherein the width of said relatively short slots exceeds the size of the diameter of said bone pins.

27. The fixator as claimed in claim 25, wherein said spherical bodies are introduced into said tubular members with their diametral holes substantially aligned with respective pairs of said relatively short slots, after which at least one of said bone pins is passed through one of said pairs of short slots via one of said spherical bodies, the length of said pairs of relatively short slots being such as to permit said bone pin to include with the axis of said tubular members angles other than 90°.

28. The fixator as claimed in claim 22, wherein the width of said pairs of slots is large enough to permit said bone pins to include with the plane defined by said diagonally opposed generatrices angles other than 0°.

29. The fixator as claimed in claim 27, wherein, after introduction of said bone pins into said tubular members via said spherical bodies and the introduction of said pins into the patient's bone, said pins are locked in said spherical bodies by elastic deformation of the latter produced by pressure-applying means with the aid of said thread means.

* * * * *